United States Patent [19]

Tarasov et al.

[11] 4,451,236

[45] May 29, 1984

[54] DENTAL PROSTHESIS AND METHOD FOR MAKING SAME

[76] Inventors: Jury A. Tarasov, ulitsa Levanevskogo, 56/10; Ljudmila V. Zhivkova, ulitsa Aviatsionnava, 19, kv. 32, both of Dnepropetrovsk; Anatoly M. Kotlyar, ulitsa Akademika Pavlova, 140G, kv. 65, Kharkov; Vasily P. Panchokha, ulitsa Furmanova, 14, kv. 26; Natalia V. Alexeenko, ulitsa Furmanova, 14, kv. 26, both of Dnepropetrovsk; Anatoly I. Grabchenko, ulitsa Pushkinskava, 74, kv. 67, Kharkov; Viktor G. Lappo, ulitsa, 7 Korpus 4, kv. 55, Moscow; Albert M. Boyarunas, ulitsa Sverdlova, 154, KV. 73, Kharkov; Vitaly F. Drozhin, ulitsa Barrikadnaya, 26, kv. 85, Kharkov; Anatoly A. Andreev, ulitsa Danilevskogo, 31, kv. 47, Kharkov; Igor V. Gavrilko, prospekt Traktorostroitelei, Kharkov; Mikhail A. Napadov, ulitsa Rollana, 9, kv. 7, Kharkov; Valentin G. Padalka, ulitsa Danilevskogo, 10, kv. 122, Kharkov; Abram L. Sapozhnikov, ulitsa Vasilevskoi, 15, kv. 52, Kiev, all of U.S.S.R.

[21] Appl. No.: 522,264

[22] Filed: Aug. 11, 1983

[51] Int. Cl.³ ............................................. A61C 5/08
[52] U.S. Cl. .................................. 433/207; 433/208; 433/218; 433/222
[58] Field of Search ..................... 433/207, 208, 218

[56] References Cited

U.S. PATENT DOCUMENTS 1,990,590  2/1935  Franks ................................ 433/207
4,181,757  1/1980  Youdelis .............................. 433/218

FOREIGN PATENT DOCUMENTS 1215485  12/1970  United Kingdom .

*Primary Examiner*—Veronica P. Hoke
*Attorney, Agent, or Firm*—Burgess, Ryan & Wayne

[57] ABSTRACT

The dental prosthesis comprises a base from a durable corrosion-resistant metallic alloy and at least one external decorative layer. The external decorative layer is made of a harder material than the base and comprises nitrides, oxynitrides, carboxynitrides, cyanonitrides and/or oxides of metals of the subordinate subgroup of Group IV of the periodic system. The thickness ratio of the external decorative layer to the base is equal to 1:10-200 respectively.

In the case where the dental prosthesis base comprises a structure of soldered members from a durable corrosion-resistant metallic alloy, the method for making the dental prosthesis comprises manufacture of the base by soldering members of the dental prosthesis from the abovementioned alloy into an integrated structure. Then the zone of the soldered juncture or the entire structure is coated, by electroplating or vacuum technique, with an additional layer from cobalt, nickel, molybdenum, chromium or zirconium, or from nitrides of chromium or molybdenum. The thickness ratio of the additional layer to the external decorative layer is equal to 0.5-1:1 respectively. Thereafter, the external decorative layer is deposited by vacuum technique.

10 Claims, No Drawings

DENTAL PROSTHESIS AND METHOD FOR MAKING SAME

FIELD OF THE INVENTION

The present invention relates to prosthetic dentistry and, more particularly, to a dental prosthesis and a method for making same.

BACKGROUND OF THE INVENTION

Known in the art are monolithic dental prostheses which are made usually either from alloys of noble metals: gold, platinum, palladium, or from various corrosion-resistant steels and alloys.

In the former case metallic dental prostheses have a high biological indifference and decorative aesthetic characteristics. However, due to a low wear resistance of alloys of noble metals these prostheses are but short-lived.

In the latter case noble metals are saved and a long service life of dental prostheses is ensured. However, dental prostheses manufactured from corrosion-resistant steels and alloys are inferior to the former in the biological indifference and aesthetic properties.

Depending on the employed structural materials the following embodiments of non-removable dental prostheses are known:

from porcelain and metal-ceramics;

from metallic alloys with a low content of noble metals:

laminated structures of dental prostheses, wherein a noble metal is used only as an external layer (coating) of the dental prosthesis.

The manufacture of metal-ceramic structures is difficult, while porcelain crowns having good decorative-aesthetic characteristics are employed for restoration of the front teeth. They have but insufficient mechanical strength due to brittleness of porcelain.

In alloys with a lower content of noble metals it is impossible to bring the content of noble metals below 40-60% without impairing their biological indifference.

Durable dental prostheses with high medico-biological properties and decorative-aesthetic characteristics can be produced only through essential reduction of noble metals for their manufacture. However, at the present time such dental prostheses cannot find an extensive application, since high medico-biological properties and decorative-aesthetic characteristics are retained only during 2-3 months of their functioning.

Known in the art is a structure of a laminate dental prosthesis (cf. British Patent Application No. 1,215,485 Cl.A61 c 13/02) produced by electroplating, wherein first deposited is a layer of a metal compatible with the organism tissues (gold, rhodium or chromium), then a second layer of a corrosion-resistant non-noble metal (nickel) more durable than the first, and a third layer of a metal (gold, rhodium or chromium) compatible with the body tissues.

Also known is a structure of a dental prosthesis (cf. USSR Inventor's Certificate No. 212442 Cl. A 61 c 5/08). This prosthesis consists of a metal base of a durable corrosion-resistant metallic alloy (a silver-palladium alloy) and an external decorative layer. The external layer comprises a gold-based alloy having smaller, as compared to the base, hardness.

These dental prostheses make it possible to reduce, by 90-95%, the rate of consumption of noble metals. However, since the layer thickness of noble metals in the prosthesis structure does not exceed 10-20 $\mu$m (at greater thickness values there is no sense in using a laminate structure of a dental prosthesis due to an increased consumption of a noble metal), the chewing faces of the prosthesis subjected to an intensive wear become rapidly (within 2-3 months of the prosthesis functioning) worn and the decorative-aesthetic effect of the dental prosthesis is lost. Furthermore, upon damaging of the external decorative layer of the dental prosthesis there occurs a sharp electrochemical impairing (change in the difference of electric potentials by 20-60 mV) of the prosthesis structure, the formation and an active functioning of microgalvanic couples. This may cause a local and general harmful effect on the human organism. At the same time, due to the presence of microgalvanic couples, the base of the prosthesis becomes rapidly deteriorating and, consequently, the process of destruction of the external decorative layer is accelerated.

SUMMARY OF THE INVENTION

It is an object of the present invention to provide such a dental prosthesis which would contain no precious metals, possess a long service life (exceeding that of monolithic prostheses based on precious alloys), while retaining, during its entire functioning term, high medicobiological properties and decorative-aesthetic properties, as well as would be simple and inexpensive in manufacture.

It is another object of the present invention to provide a method for making said dental prosthesis.

These and other objects of the present invention are accomplished by dental prosthesis consisting of a base comprising a durable corrosion-resistant metallic alloy and at least one external decorative layer, wherein, according to the present invention the external decorative layer is embodied of a harder material as compared to the base and comprises nitrides, oxynitrides, carboxynitrides, cyanonitrides and/or monoxides of metals of the subordinate subgroup of Group IV of the periodic system, the thickness ratio of the external decorative layer to the base being equal to 1:10-200 respectively.

The prosthesis base is made of a durable corrosion-resistant material: stainless steel, chrome-cobalt, chrome-nickel-molybdenum or any other conventional metal alloy. Such base imparts a high mechanical strength to the dental prosthesis at sign-changing loads originating in chewing a food. The dental prosthesis base can be monolithic or assembled from individual structural members rigidly secured to one another by welding or soldering.

Nitrides, oxynitrides, carboxynitrides, cyanonitrides and/or monoxides of metals of the subordinate subgroup of Group IV of the periodic system, wherefrom the external decorative layer of the prostheses according to the present invention is made, have a high chemical resistance in acidic, alkaline and neutral media of the mouth cavity, non-toxicity and good toleration by the organism tissues. For this reason, the prostheses per se are also resistant in the mouth cavity media and biologically indifferent.

As the material of the external decorative layer according to the present invention it is advisable to use nitrides, oxynitrides, carboxynitrides, cyanonitrides and/or monoxides of titanium and/or zirconium.

Since nitrides, oxynitrides, carboxynitrides, cyanonitrides and/or monoxides of titanium and/or zirconium have a wide range of golden-yellow, golden, golden-red and silvery shades and colours (depending on the type of a chemical compound and parameters of the process of its preparation), when applied onto metallic articles these compounds ensure a required decorative-aesthetic effect. Thus, zirconium nitride, depending on the content of nitrogen therein, has a silvery to dark-golden colour, i.e. imitates platinum or gold alloy. Titanium nitride, mixtures of titanium nitride and zirconium nitrides, monoxides of titanium and/or zirconium and oxynitrides thereof can have golden-straw, golden-yellow and golden-red colours and a plurality of their shades, thus imitating gold of different purity standards and widening the range of obtained colour shades.

The hardness of the materials employed for the manufacture of the external decorative layer of the dental prostheses according to the present invention amounts to $10^4$ MPa (2,200–2,900 kgf/mm$^2$) which is substantially higher than the hardness of conventional metallic alloys employed in stomatology. For this reason, the external decorative layer of such prosthesis features a high wear-resistance (by 180–220 times higher than the wear-resistance of an electroplated gold layer) and enables a high resistance of the dental prosthesis against wear.

An increased brittleness of the materials employed for the manufacture of the external decorative layer imposes certain limitations on the thickness ratio between the base and the external layer. The thinner is the external decorative layer, the higher is plasticity thereof. However, an extensive thinning of this layer shortens the service life of the dental prosthesis due to a rapid abrasion thereof.

It has been experimentally found that the thickness ratio between the external decorative layer and the prosthesis base should be within the range of from 1:10 to 1:200. In the case of bridge-like or clasp prostheses the thickness calculation for the decorative layer should be effected for the thinnest cross-section of the prosthesis structure.

The external decorative layer of the dental prosthesis according to the present invention, depending on the functions to be performed, can be single-layered, two-layered or multi-layered. In a multi-layer composition of the external decorative layer use may be made of alternating layers of the above-mentioned metallic compounds of titanium and zirconium. Multi-layered compositions of the external decorative layer enable a broad variation of its adhesion characteristics relative to the substrate from different materials, increase characteristics of plasticity and wear-resistance of the decorative layer and enlarge the range of its colour shades.

The dental prostheses according to the present invention can be applicable to the following range of articles: single stamped and cast crowns (full-size, equatorial, half-crowns, three-quarter crowns, pinned crowns), whole-cast bridge-like prostheses, soldered bridge-like dental prostheses with cast false teeth and facets, cast inserts, clamps for fixation of dental prostheses in the case of parodontosis, as well as carcasses and arches of clasp prostheses, bent and cast klammers.

At an insignificant deterioration of the integrity of the external decorative layer (availability of micropores or microcracking, local wear) not affecting the decorative-aesthetic properties of the dental prostheses, microgalvanic couples can be formed between the base and the external decorative layer due to the filling of the above-mentioned defects with the liquid media of the mouth cavity.

The consequence of functioning of microgalvanic couples (without special measures to be taken) is the origination and development of corrosion foci of a more electronegative metal of the couple, i.e. the base of the dental prosthesis. This results in a local breaking of the base under the coating, an accelerated destruction of the weakened (no support) external decorative layer due to mechanical forces and, eventually, in loss of decorative-aesthetic properties of the dental prosthesis.

To improve corrosion protection of the material of the base of the dental prosthesis according to the present invention, it is advisable to place, between the prosthesis base and the external decorative layer, a protective layer of a metal more electronegative than the material of the external decorative layer and capable of being passivated in liquid media of the mouth cavity; the thickness ratio between the protective layer and the external decorative layer being equal to 0.3-1:1.

In the presence of this protective layer, in the case of defects of integrity of the external decorative layer, the liquid medium of the mouth cavity gets access not to the prosthesis base, but to the material of the protective layer. A microgalvanic couple is formed between the metals of the protective and external decorative layers. The role of anode in this couple is played by a more electronegative metal, i.e. the protective layer metal. But the metal of the protective layer is selected so as to ensure its rather good passivation under the conditions of anodic polarization. In the zone of the defect of the external decorative layer there always occurs anodic polarization due to the difference of electric potentials of the contacting metals, i.e. the protective layer has all conditions for its passivation (formation of passive films). The protective layer, having passive films, stops a further distruction (dissolution) of the metal of this layer, thus preventing corrosion processes. This ensures corrosion resistance of the dental prosthesis according to the present invention.

As the metal of the protective layer it is advisable to use titanium, tantalum, or chromium. These metals are capable of being easily passivated in media of the mouth cavity, thus preventing the protective layer from corrosion destruction and, hence, the base of the dental prosthesis accordingly.

To ensure a reliable protection of the metal alloy of the dental prosthesis base from corrosion, the protective layer should be solid (i.e. without through pores). Since with increasing thickness of the layer the probability of presence of through pores therein is reduced, the protective layer should be made to a maximum possible thickness. However, with increasing thickness of the protective layer the difficulties associated with its deposition are aggravated. From this point of view the protective layer should be made to a minimum possible thickness.

It has been experimentally found that the ratio of the protective layer thickness to the external decorative layer thickness should be 0.3-1:1 respectively. Lesser values are used for tantalum and titanium, greater for chromium.

Physico-mechanical characteristics (thermal coefficient of linear expansion, plasticity, microhardness and the like) of the base and the external decorative layer differ substantially (by several times).

Upon variation of temperature conditions or mechanical loads, e.g. during functioning of the dental prosthesis, at the interface of the above-mentioned layers there occurs concentration of mechanical stresses. In some cases this even causes peeling of the external decorative layer.

To avoid this, in the dental prosthesis according to the present invention between the base and the external decorative layer or between the protective and external decorative layers it is advisable to interpose a transition layer consisting of titanium, tantalum or chromium in a mixture with a corresponding metal nitride. The concentration of these nitrides is increased across the transition layer thickness in the direction towards the external layer within the range of from 0.01 to 90-99.9% by weight and the thickness ratio of the transition layer to the external decorative layer is 0.3-1:1.

Owing to the above-mentioned distribution of concentration of metals and their nitrides in the transition layer there is ensured a gradual variation of physicomechanical characteristics of this layer. Values of the transition layer characteristics are varied across its thickness in the range of from the values of the base characteristics to the values of the characteristics of the external decorative layer.

In stomatological practice, where bridge-like dental prostheses are manufactured, use is frequently made of soldered structures of a dental prosthesis base. Members of such a structure (crowns, facet carcasses, false teeth) are made separately and then assembled into an integrated structure by soldering methods.

Where structural members of dental prostheses from stainless steel, chromium-cobalt and other conventional corrosion-resistant metal alloys are to be soldered, inexpensive silver solders are effectively employed. Most frequently used among them are silver-cadmium solders (composition, percent by mass: Ag-45, Cu-25, Cd-15 and Mn-15) with a melting point ranging from 620° to 660° C., or silver-zinc solders (in the USSR they have the following composition, in percent by mass: Ag-63, Cu-27, Zn-10; in Federal Republic of Germany they have the following composition: Ag-37, Cu-38, Zn-15, Cd-0.5, Mn-5.2, Ni-4, Mg-0.3) with a melting temperature ranging from 800° to 850° C.

At the points of soldering the external decorative layer usually deposited within the temperature range of 400° to 500° C. and above, has a lowered adhesion due to evaporation of individual components of the solder. This frequently causes peeling of the external decorative layer or the formation of cracks therein, as well as pores and other defects at the points of soldering.

Therefore, where the base of a dental prosthesis comprises a structure of soldered members of a durable corrosion-resistant metallic alloy between the external decorative layer and the dental prosthesis base or between the transition layer and the dental prosthesis base it is advisable to provide an additional layer. In the former case, this additional layer is preferably made from cobalt, nickel, chromium, molybdenum or zirconium, or from nitrides of chromium or molybdenum. In the latter case the additional layer is preferably made from cobalt, nickel, chromium, molybdenum or zirconium. In both cases the thickness ratio of the additional layer to the external decorative layer is 0.5-1:1 respectively.

With a thickness ratio of the additional layer to the external decorative layer being 0.5-1:1, the additional layer has no through pores. The poreless additional layer is a sufficiently reliable barrier not only for the liquid, but for the vapour phase of the evaporated solder components as well. A greater thickness of the additional layer is inexpedient due to greater costs of manufacture of this layer.

Providing an additional layer in a soldered structure of the base of a dental prosthesis would ensure integrity of the soldered seam, absence of visible pores at the points of soldering and, consequently, a high quality of their external decorative layer, including the zone of the soldered seam.

In a process for the manufacture of such a dental prosthesis involving manufacture of a base by way of soldering members of a dental prosthesis from a durable corrosion-resistant metal alloy into an integrated structure and application of an external decorative layer by vacuum technique, according to the present invention, the zone of the soldered juncture of this structure or the entire structure is coated, prior to deposition of the external decorative layer, by electroplating or vacuum technique with an additional layer from cobalt, nickel, chromium, molybdenum or zirconium or from nitrides of chromium or molybdenum, the thickness ratio of this layer to the external decorative layer being 0.5-1:1.

As mentioned above, the additional layer eliminates the appearance of defects in the external decorative layer at soldered seams and increases mechanical strength of the soldered juncture.

The dental prostheses according to the present invention compare favourably with monolithic dental prostheses made from alloys of gold or platinum in their decorative-aesthetic characteristics, biological indifference, chemical and corrosion resistance, whereas in mechanical strength and wear-resistance they are even superior to them. The dental prostheses according to the present invention are more simple in manufacture and economically more efficient. They are by 10-15 times less expensive than dental prostheses manufactured from gold alloys, porcelain or metal-ceramics.

Prostheses with the external layers according to the present invention are resistant to the effect of common salt and saliva, indifferent to cultures of blue pus bacillus, staphylococcus aureus, colibacillus, primary-trypsinized cultures of cells of human embryo fibroplasts, grafted line of cells HEP-2 and cells of human bucal epithelium.

The external decorative layer in the dental prostheses according to the present invention causes no chromosomal aberrations.

DETAILED DESCRIPTION OF THE INVENTION

The method for the manufacture of dental prostheses according to the present invention is simple, based on known processes and can be performed in the following manner.

First to be made is the base of a dental prosthesis following procedures commonly known in stomatology (precise casting and stamping) from durable corrosion-resistant non-noble alloys (stainless steels, alloys of cobalt and chromium or cobalt, chromium and molybdenum) in the form of blanks of an appropriate shape. Then, the precision of their setting in the patient's mouth is checked. After fitting and adjustment, scaling is removed from the blank surfaces and the blank is polished to the surface roughness of $R_z = 0.1$ to $0.4 \ \mu m$. Then the base of the dental prosthesis is thoroughly washed following the conventional procedure and degreased in an ultrasound bath.

Using known methods of vacuum technique an external decorative layer is deposited to a calculated thickness from a material ensuring its adherence and wear-resistance, a well as a required colour and shade of the coating. As it has been already mentioned hereinabove, the external decorative layer can consist of a single layer, two or more sublayers. In the case of deposition of two and more layers, the composition and pressure of the reaction gas, evaporated material and process parameters of deposition of the layers are varied depending on particular tasks to be achieved.

Thereafter, the eternal decorative surface of the dental prosthesis is polished, when required, and, if necessary, lacking members are shaped on the prosthesis from plastics.

Where a protective layer is required in the dental prosthesis, a layer from titanium, tantalum or chromium is deposited to a required thickness by one of the known methods (electroplating, vacuum-plasma treatment) prior to application of the external decorative layer.

As mentioned above, to lower concentration of mechanical stresses at the interphase between the base and the external decorative layer or between the external decorative layer and the protective layer, a transition layer is formed. The transition layer is deposited also by a known, e.g. vacuum-plasma, method increasing pressure of nitrogen in the chamber during deposition of the layer.

If the base of the dental prosthesis is a soldered structure, onto such (soldered) dental prosthesis an additional layer of a calculated thickness from cobalt, nickel, chromium, molybdenum, zirconium, nitrides of chromium or molybdenum is deposited prior to the operations of the vacuum-plasma deposition of the layers (protective, transition, external decorative).

For a better understanding of the present invention the following specific examples are given hereinbelow by way of illustration.

EXAMPLE 1

A dental prosthesis is made in the form of a monolithic bridge-like structure comprising a base of a chromium-cobalt alloy with an external decorative layer from titanium nitride.

The base of the dental prosthesis is cast to the required shape from a chromium-cobalt alloy using a wax pattern. The precision of its setting in the patient's mouth is checked and the base is finally adjusted. The adjusted base of the dental prosthesis is polished by means of finely-divided (0.5–1 $\mu m$) abrasive compositions. After polishing the prosthesis base is thoroughly washed in an ultrasonic bath with a hot (70°–80° C.) water containing 2–3% by mass of synthetic detergents. Then rinsing is effected with running water, in a bath with gasoline, degreasing is effected with ethanol.

Thereafter, the base of the bridge-like dental prosthesis is placed into a chamber of a vacuum unit provided with a pivotting device having a drum on which the base is placed. The chamber is also provided with three sources of titanium plasma directed towards the drum of the pivotting device. As the evaporated material in all three plasma sources use is made of chemically pure titanium.

The vacuum chamber is evacuated to the pressure of $1.10^{-5}$ mm Hg, the turning or pivotting device is switched on (rotating speed is 9 r.p.m.), a negative voltage of 1.1 kV is applied to the base, one plasma source is energized and the arc current in it is fixed at 80 A. A full purification of the base is effected for 3 minutes by bombardment thereof with titanium ions. Then a negative voltage of 180 V is applied to the base and the second and third plasma sources are switched on. The arc current in each of the three sources is 90 A. Under these conditions nitrogen is admitted into the chamber and its pressure therein is set at $5 \times 10^{-3}$ mm Hg. An external decorative layer of titanium nitride is deposited on the base. When the thickness of this layer reaches 8 $\mu m$, the plasma sources are switched-off, the supply of nitrogen is discontinued, the turning device is stopped, the negative voltage is removed from the prosthesis and 10 minutes thereafter the prosthesis is extracted from the chamber.

The external decorative layer has a microhardness of from 2,500 to 2,600 $kgf/mm^2$ and colour corresponding to the colour of a high-purity gold and a good adhesion to the base.

The thus-produced prosthesis is fixed in the patient's mouth cavity by means of a bisphate cement. Observations for 4 years revealed no local and general negative effects on the organism. The integrity of the prosthesis was not damaged. The prosthesis colour was not changed.

EXAMPLE 2

A dental prosthesis is made in the form of a monolithic bridge-like structure comprising a base of a chromium-cobalt alloy with an external decorative layer of titanium oxynitride.

The dental prosthesis base is made, polished, rinsed and placed in a vacuum chamber as described in the foregoing Example 1.

The treatment of the dental prosthesis base to the moment of the supply of nitrogen into the vacuum chamber is also effected as described in Example 1. Instead of nitrogen fed into the vacuum chamber is a mixture of nitrogen and oxygen (80% by volume of nitrogen and 20% by volume of oxygen) and the pressure inside the chamber is set at $5 \times 10^{-3}$ mm Hg. A layer of titanium oxynitride is deposited on the base surface. When the thickness of this layer is made equal to 10 $\mu m$, the plasma sources are switched-off, the supply of the above-identified gas mixture is stopped, the negative voltage is removed from the prosthesis and the turning device is also switched-off. 10 minutes thereafter the prosthesis is removed from the chamber.

The external decorative layer has the microhardness of 2,300 $kgf/mm^2$, the colour corresponds to the colour of a high-purity gold alloy, it also has a good adhesion to the base.

The thus-produced dental prosthesis is fixed in the patient's mouth cavity by means of a bisphate cement. Observations for 2 years revealed no local or general negative effects on the organism. The prosthesis colour remained unchanged.

EXAMPLE 3

A dental prosthesis is made in the form of a monolithic bridge-like structure comprising a base from a chromium-cobalt alloy with an external decorative layer from zirconium nitride.

The dental prosthesis base is made, polished, rinsed and placed into a vacuum chamber following the procedure described in Example 1 hereinbefore.

The vacuum chamber is provided with three plasma sources, wherein the evaporated metal is zirconium. The ionic purification by bombardment with ions of zirconium and application of the external decorative layer of zirconium nitride are effected as described in Example 1. The layer deposition is effected to the thickness of 20 μm.

The resulting layer has the microhardness of 2,500 kgf/mm² the colour corresponding to that of a high-purity gold alloy and a good adhesion to the base.

The thus-produced prosthesis is fixed in the patient's mouth cavity by means of bisphate cement. Observations for four years revealed no local or general negative effects on the patient's organism.

EXAMPLE 4

A dental prosthesis is made in the form of a monolithic bridge-like structure comprising a base from a chromium-cobalt alloy with an external decorative layer from nitrides of titanium and zirconium (70% by weight of titanium nitride and 30% by weight of zirconium nitride).

The dental prosthesis base is manufactured, polished, rinsed and placed into a vacuum chamber following the procedure described in Example 1 hereinbefore.

The vacuum chamber is provided with three plasma sources wherein one of the evaporated materials is zirconium (one source); in two other sources the evaporated material is titanium. The ion purification of the base is carried out as described in Example 1.

Then the negative voltage of 200 V is applied to the base, the sources of titanium and zirconium plasma are switched-on, in the sources of titanium plasma the arc current is set at 90 A, in the source of zirconium plasma—80 A. Thereafter, nitrogen is fed into the vacuum chamber and its pressure is made equal to $5 \times 10^{-3}$ mm Hg. The external decorative layer consisting of a mixture of nitrides of titanium and zirconium is deposited on the base surface (70% by weight of titanium nitride and 30% by weight of zirconium nitride). When the thickness of this layer reaches 12 μm, the plasma sources are switched-off, nitrogen supply is discontinued, turning device is stopped, the voltage is removed from the dental prosthesis and 10 minutes thereafter the dental prosthesis is withdrawn from the vacuum chamber.

The external decorative layer has the microhardness of 2,600 kgf/mm²; its colour corresponds to that of high-purity gold alloy, it also has a good adhesion to the base.

The thus-produced dental prosthesis is fixed in the patient's mouth cavity by means of a bisphate cement. Observations for four years revealed no local or general negative effects on the patient's organism. No zirconium and titanium were detected in analysis of the patient's saliva. The prosthesis colour remained unchanged.

EXAMPLE 5

A dental prosthesis is made in the form of a bridge-like monolithic structure comprising a base from a chromium-cobalt alloy with an external decorative layer from a mixture of nitrides of titanium and zirconium (0.1% by weight of zirconium nitride and 99.9% by weight of titanium nitride).

The dental prosthesis base is made, polished, rinsed and placed into a vacuum chamber as described in Example 1.

The vacuum chamber is provided with three plasma sources, wherein as the evaporated material use is made of an alloy consisting of 99.9% by weight of titanium and 0.1% by weight of zirconium.

Application of the external decorative layer is carried out as described in Example 1 to the thickness of 15 μm. The resulting layer has the microhardness of 2,500 kgf/mm²; its colour matches that of a high-purity gold alloy; it also has a good adhesion to the base.

The thus-produced prosthesis is fixed in the patient's mouth cavity by means of bisphate cement. Observations for four years revealed no local or general negative effects on the patient's organism. The prosthesis colour remained unchanged.

EXAMPLE 6

A dental prosthesis is made in the form of a monolithic bridge-like structure comprising a base from a chromium-cobalt alloy with an external decorative layer consisting of two sublayers of which one is adjacent to the base consists of a mixture of carboxynitrides of titanium and zirconium (67% by weight of titanium carboxynitride and 33% by weight of zirconium carboxynitride), the second - from titanium nitride.

The dental prosthesis base is made, polished, washed and placed into a vacuum chamber as described in Example 1. The vacuum chamber is provided with three plasma sources, in one of which zirconium is used as the evaporated material, in two others - titanium. The ion purification of the base is effected as described in Example 1.

Then, a negative voltage of 200 V is applied to the base, plasma sources with titanium and zirconium are switched-on, in each of the plasma sources the arc current is set at 90 A. Then, a mixture of nitrogen, oxygen and methane (80% by volume of nitrogen, 10% by volume of oxygen and 10% by volume of methane) is fed into the vacuum chamber and its pressure in the vacuum chamber is set at $1 \times 10^{-3}$ mm Hg. On the base surface there is deposited a first sublayer of the external decorative layer consisting of a mixture of titanium and zirconium carboxynitrides (67% by weight of titanium carboxynitride and 33% by weight of zirconium carboxynitride).

When the thickness of this sublayer reaches 6 μm, the plasma source of zirconium is switched-off, the supply of this gas mixture is discontinued and nitrogen is passed into the chamber to keep its pressure therein at $5 \times 10^{-3}$ mm Hg. A second sublayer of the external decorative layer is thus deposited from titanium nitride.

When the thickness of the titanium nitride sublayer reaches 3 μm, the plasma sources are switched-off, the supply of nitrogen is discontinued, the negative voltage is removed from the prosthesis and the turning device is stopped. After 10 minutes the prosthesis is withdrawn from the chamber.

The resulting external decorative layer has microhardness of 2,600 kgf/mm², its colour corresponds to that of high-purity gold alloys and the layer has a good adherence to the base.

The thus-produced dental prosthesis is fixed in the patient's mouth cavity by means of a bisphate cement. Observations for four years revealed no local or general negative effects on the patient's organism. The prosthesis colour remained unchanged.

EXAMPLE 7

A dental prosthesis is made in the form of a monolithic bridge-like structure comprising a base from a chromium-cobalt alloy with an external decorative layer consisting of two plies one of which adjacent to the base consists of titanium cyanonitride and the second - from titanium oxynitride.

The base of the dental prosthesis is manufactured, polished, rinsed and placed into a vacuum chamber as described in Example 1 hereinbefore.

The treatment of the dental prosthesis base is effected, till the moment of admitting nitrogen into the vacuum chamber, as described in Example 1. Instead of nitrogen fed into the vacuum chamber is a mixture of nitrogen and acetylene (95% by volume of nitrogen and 5% by volume of acetylene) and the pressure in the vacuum chamber is maintained at $8 \times 10^{-4}$ mm Hg. A layer of titanium cyanonitride is deposited on the surface of the prosthesis base. After deposition of this layer to the thickness of 5 μm, the supply of the above-specified gas mixture is discontinued, and the gas mixture composed of nitrogen and oxygen (90% by volume of nitrogen and 10 % by volume of oxygen) is fed into the vacuum chamber, wherein the pressure is maintained at $6 \times 10^{-3}$ mm Hg and a layer of titanium oxynitride is deposited. When the thickness of the layer of titanium oxynitride reaches 5 μm, the plasma sources are switched-off, the supply of the gas mixture is discontinued, the negative voltage is removed from the prosthesis and the turning device is stopped. 10 minutes thereafter the prosthesis is withdrawn from the vacuum chamber.

The resulting external decorative layer has microhardness of 2,400 kgf/mm$^2$, a colour corresponding to that of high-purity gold alloys and a good adhesion to the base.

The thus-produced dental prosthesis is fixed in the patient's mouth cavity by means of a bisphate cement. Observations for two years revealed no local and general negative effects on the patient's organism. The prosthesis colour remained unchanged.

EXAMPLE 8

A dental prosthesis is made in the form of a monolithic bridge-like structure comprising a base from a chromium-cobalt alloy with an external decorative layer consisting of two plies one of which adjacent to the base consists of titanium oxide, the second - from titanium nitride.

The dental prosthesis base is made, polished, rinsed and placed into the vacuum chamber as described in Example 1.

The treatment of the dental prosthesis base till the moment of nitrogen admission into the vacuum chamber is also effected following the procedure of Example 1.

Instead of nitrogen into the vacuum chamber oxygen is fed and its pressure therein is maintained at $5 \times 10^{-4}$ mm Hg. On the base surface a layer of titanium monoxide is deposited. When the thickness of this layer reaches 5 μm, the oxygen supply is discontinued and nitrogen is admitted into the chamber and its pressure is maintained at $5 \times 10^{-3}$ mm Hg; a second ply of titanium nitride is deposited. When the thickness of the ply of titanium nitride reaches 5 μm, the plasma sources are switched-off, the supply of nitrogen is discontinued, the negative voltage is removed from the prosthesis and the turning device is stopped. 10 minutes thereafter the prosthesis is withdrawn from the chamber.

The resulting external decorative layer has microhardness of 2,500 kgf/mm$^2$, a colour corresponding to that of high-purity gold alloys and a good adhesion to the base.

The thus-manufactured dental prosthesis is fixed in the patient's mouth cavity by means of bisphate cement. Observations for two years revealed no local and general negative effects on the patient's organism.

EXAMPLE 9

A dental prosthesis is made in the form of a monolithic bridge-like structure comprising a base from a chromium-cobalt alloy with an external decorative coating from a mixture of nitrides of titanium and zirconium (33% by weight of zirconium nitride and 67% by weight of titanium nitride) with a protective layer of titanium.

The dental prosthesis base is made, polished, rinsed and placed into a vacuum chamber as described in Example 1.

The ionic purification of the base is carried out by way of bombardment with titanium ions as described in Example 1. Then the negative voltage of 200 V is applied to the base, the second plasma source with titanium is energized, the arc current therein is set at 80 A and a protective coating of titanium is applied to the thickness of 3 μm. Then the third plasma source with zirconium is switched-on, in all of the three plasma sources the arc current is set at 90 A and nitrogen is admitted into the chamber to maintain its pressure therein at $5 \times 10^{-3}$ mm Hg. The external decorative layer is deposited from a mixture of nitrides of titanium and zirconium. When the thickness of this layer reaches 10 μm, the plasma sources are switched-off, the supply of the gas mixture is discontinued, the negative voltage is removed from the prosthesis and the turning device is stopped.

The technical and medical characteristics of the thus-produced dental prosthesis are similar to those described in Example 4 hereinbefore.

EXAMPLE 10

A dental prosthesis is made in the form of a single crown from stainless steel with an external decorative layer from titanium nitride and a protective layer from tantalum. A cylindrical sleeve from a stainless steel is heated to a temperature within the range of from 800° to 900° C. and stamped to produce a crown blank of a desired shape. Then the blank is subjected to a high-temperature annealing, the precision of the blank setting on the tooth stump is checked and the final adjustment is made according to the occlusion of the antagonist tooth.

Then scaling is removed from the crown by placing it into a solution of the following composition, g/l: sulphuric acid - 100, nitric acid - 150, hydrofluoric acid - 30. In the solution the blank is kept till complete removing of the scale (20-60 seconds). Then the blank is rinsed in running water, dried and polished by means of finely-divided abrasive compositions (0.5-1 μm fineness). The resulting prosthesis base is washed in an ultrasound bath with hot (70°-80° C. )water containing 3% of synthetic detergents and then with gasoline and ethanol. Then the prosthesis base is placed into a chamber of a vacuum unit onto the drum of a turning device. The vacuum chamber is provided with three plasma sources; in one of them the evaporated material is tantalum, in the two others - titanium.

The vacuum chamber is evacuated to the pressure of $1.10^{-5}$ mm Hg, the turning device is started, the negative voltage of 800 V is applied to the base and the plasma source of tantalum is switched-on and the arc current thereof is set at 200 A.

The ionic purification of the base is effected by means of bombardment with tantalum ions for 2 minutes. Then the negative voltage of 50 V is applied to the base and a protective layer of tantalum is deposited. When the protective layer thickness reaches 3 $\mu$m, two plasma sources of titanium are switched-on with the arc current in each of them set at 90 A, the plasma source of tantalum is switched-off, the negative voltage of 180 V is applied to the base and nitrogen is fed into the chamber; its pressure therein is maintained at $5 \times 10^{-3}$ mm Hg to deposit the external decorative layer of titanium nitride. When this layer thickness reaches 9 $\mu$m, the plasma sources are switched-off, the supply of nitrogen is discontinued, the negative voltage is removed and the turning device is stopped. After 10 minutes the prosthesis is withdrawn from the chamber.

The resulting external decorative layer has microhardness of 2,500 kgf/mm$^2$, a colour corresponding to that of high-purity gold alloys, a high wear-resistance (by 190 times higher than that of gold alloys).

The thus-produced prosthesis is fixed in the patient's mouth cavity by means of bisphate cement. Observations for four years revealed no local or general negative effects on the patient's organism. The prosthesis colour was not changed.

EXAMPLE 11

A dental prosthesis is produced in the form of a soldered bridge-like structure comprising a base from a chromium-nickel stainless steel and a silver-cadmium solder with a protective layer of chromium and an external decorative layer from a mixture of nitrides of titanium and zirconium (0.5% by weight of zirconium nitride and 99.5% by weight of titanium nitride).

Blanks of crowns of the bridge-like dental prosthesis are made as described in Example 10 hereinbefore. Then the intermediate portion of the prosthesis is cast according to the wax pattern (facets and false teeth) and an integrated structure of the base of the bridge-like prosthesis is obtained by soldering using a silver-cadmium solder. Then scaling is removed, the blank is polished and washed as described in Example 10.

Then the base is submerged into a galvanic bath for deposition of a protective layer by chromium-plating.

As the aqueous electrolyte for chrome-plating use is made of the following composition, g/l: chromic anhydride- 250, sulphuric acid 2,5. The deposition is effected at a temperature of the electrolyte of 60° C. and a current density of 50 A/dm$^2$. Under these conditions a protective chromium layer is deposited to the thickness of 8 $\mu$m.

Then the base with the protective chromium coating is polished by means of finely-divided diamond pastes, washed in an ultrasound bath with hot water containing 3% by mass of synthetic detergents, gasoline and ethanol.

Thereafter the base is placed into a vacuum chamber on a drum of a turning device. The vacuum chamber is provided with three plasma sources, wherein as the evaporated material use is made of an alloy of titanium and zirconium (0.5% by weight of zirconium and 99.5% by weight of titanium).

The ionic purification of the base by bombardment with titanium and zirconium ions and application of the external decorative layer from a mixture of nitrides of titanium and zirconium with the thickness of 8 $\mu$m are effected as described in Example 1.

The thus-produced prosthesis has technical and medical characteristics similar to those described in Example 5.

EXAMPLE 12

A dental prosthesis is made in the form of a monolithic bridge-like structure comprising a base from a chromium-cobalt alloy with an external decorative layer from titanium oxynitride and a transition layer from a mixture of titanium and titanium nitride. The dental prosthesis base is made, polished, washed and placed into a vacuum chamber as described in Example 1.

The vacuum chamber is provided with three plasma sources, wherein as the evaporated material use is made of titanium.

The ionic treatment of the base is effected as described in Example 1. Then the negative voltage of 200 V is applied to the base, the arc current therein is set at 80 A and nitrogen is fed into the chamber while progressively increasing its pressure from $1 \times 10^{-5}$ mm to $1 \times 10^{-4}$ mm Hg during the entire time of deposition of a transition layer with the thickness of 6 $\mu$m. The content of titanium nitride in the transition layer is increased from 0.01 to 90% by weight across its thickness.

When the transition layer thickness reaches 6 $\mu$m, the supply of nitrogen is discontinued and a mixture of nitrogen and oxygen (85% by volume of nitrogen and 15by volume of oxygen) is admitted into the chamber and the pressure of $5 \times 10^{-3}$ mm Hg is maintained therein. The external decorative layer thus deposited has the thickness of 25 $\mu$m.

Technical and medical characteristics of the thus-produced prosthesis correspond to the characteristics specified in Example 2.

EXAMPLE 13

A dental prosthesis is made in the form of a monolithic bridge-like structure comprising a base from a chromium-cobalt alloy with an external decorative layer from a mixture of titanium nitride and zirconium nitride (50% by weight of titanium nitride and 50% of zirconium nitride) and a transition layer from a mixture of tantalum nitride.

The prosthesis base is made, polished, washed and placed into a vacuum chamber as described in Example 1 hereinbefore.

The vacuum chamber is provided with three plasma sources; in one of them as the evaporated material use is made of tantalum; in the second - titanium and in the third - zirconium.

The ionic purification is effected as described in Example 10. Then a negative voltage of 100 V is applied to the prosthesis base and nitrogen is admitted into the chamber, while increasing gradually its pressure from $1 \times 10^{-5}$ to $8 \times 10^{-4}$ mm Hg during the entire period of deposition of the transition layer to the thickness of 4 $\mu$m. The content of tantalum nitride in the transition layer across its thickness is increased from 0.01 to 95% by weight. When the transition layer thickness reaches 4 $\mu$m, plasma sources with titanium and zirconium are switched-on, the arc current is set at 90 A, the plasma source with tantalum is switched-off and the negative voltage of 250 V is applied onto the base. Then nitrogen is fed into the chamber and its pressure is set at $4 \times 10^{-3}$ mm Hg and an external decorative layer is deposited from a mixture of nitrides of titanium and zirconium. When the thickness of this layer reaches 9 μm, the plasma sources are switched-off, the supply of nitrogen is discontinued, the negative voltage is removed from the prosthesis and the turning device is stopped. 10 minutes thereafter the prosthesis is withdrawn from the chamber.

Technical and medical characteristics of the thus-produced dental prosthesis are similar to those given in Example 6.

EXAMPLE 14

A dental prosthesis is manufactured in the form of a soldered bridge-like structure comprising a base from a chromium-nickel stainless steel and a silver-zinc solder with an external decorative layer from titanium nitride and a transition layer from a mixture of chromium and chromium nitride.

The prosthesis base is made, washed as described in Example 11 hereinbefore. Then the base is placed into a vacuum chamber onto a turning device drum. The vacuum chamber is provided with three plasma sources; in one of them as the evaporated material use is made of chromium, in two others - titanium.

The vacuum chamber is evacuated to the pressure of $1 \times 10^{-5}$ mm Hg, the turning device is switched on, the negative voltage of 700 V is applied to the base, the plasma source of chromium is switched-on with the arc current set at 70 A and ionic purification is effected for 4 minutes.

Then the negative voltage of 30 V is applied to the base, the arc current in the plasma source is set at 90 A and nitrogen is fed into the chamber. The pressure of nitrogen is gradually increased from $1 \times 10^{-5}$ to $3 \times 10^{-4}$ mm Hg during the entire period of deposition of the transition layer with the thickness of 4 μm. The concentration of chromium nitride is increased across the transition layer thickness from 0.01 to 90% by weight. The microhardness of this layer is increased respectively from 400 to 2,600 kgf/mm². When the transition layer thickness reaches 4 μm, two plasma sources of titanium are switched-on, the arc current in each of them is set at 90 A, the negative voltage of 180 V is applied to the base and the chromium plasma source is switched-off. Then nitrogen is fed into the chamber and its pressure of $5 \times 10^{-3}$ mm Hg is maintained therein. The external decorative layer is deposited from titanium nitride to the thickness of 10 μm. When this layer thickness reaches 10 μm, the supply of nitrogen is discontinued, the voltage on the prosthesis is removed and the turning device is stopped.

The thus-produced prosthesis has technical and medical characteristics corresponding to those of Example 1.

EXAMPLE 15

A dental prosthesis is made in the form of a soldered bridge-like structure comprising a base from a chromium-nickel stainless steel and a silver-zinc solder with an external decorative layer from zirconium nitride, a transition layer from a mixture of chromium and chromium nitride and a protective layer from chromium.

The prosthesis base is manufactured, washed as described in Example 11 hereinbefore.

Then the base is placed onto a turning device drum in a vacuum chamber.

The vacuum chamber is provided with three plasma sources in one of which as the evaporated material use is made of chromium, in two others - zirconium.

The ionic treatment of the base is effected as described in Example 14.

Then the negative voltage of 30 V is applied to the base, the arc current in the plasma source is set at 90 A and a protective layer of chromium is deposited to the thickness of 4 μm.

On reaching of the desired protective layer thickness a transition layer is deposited as described in Example 14.

The deposition of the external decorative layer is carried out as described in Example 15, with the only exception that as the evaporated metal use is made of zirconium.

The resulting external decorative layer of the prosthesis has the microhardness of 2,500 kgf/mm², a colour matching that of a high-quality gold alloy and a good adherence of the layers to one another and the base.

The thus-produced prosthesis is fixed in the patient's mouth cavity by means of a bisphate cement. Observations during four years revealed no local or general negative effects on the patient's organism.

EXAMPLE 16

A dental prosthesis is made in the form of a bridge-like monolithic structure comprising a base from a chromium-cobalt alloy with an external decorative layer consisting of a sublayer of titanium carboxynitride and a sublayer of titanium oxynitride, a transition layer of a mixture of titanium and titanium nitride, and a protective layer from titanium.

The prosthesis base is manufactured, polished, washed and placed into the vacuum chamber as described in Example 1.

The vacuum chamber is provided with three plasma sources with titanium employed as the evaporated material.

The ionic treatment of the base is carried out as described in Example 1 hereinbefore.

Then the negative voltage of 180 V is applied to the base, two other plasma sources are switched-on, the arc current in each of them is set at 80 A and the protective layer is deposited to the thickness of 6 μm. Then the transition layer is deposited from a mixture of titanium and titanium nitride as described in Example 12, with the only exception that the pressure of nitrogen is increased to $7 \times 10^{-4}$ mm Hg. This, in turn, results in an increased content of titanium nitride at the boundary with the external decorative layer to 99% by weight. When the transition layer thickness reaches 6 μm, The supply of nitrogen is discontinued, the arc current in the plasma sources is increased to 90 A and a gas mixture of nitrogen, methane and oxygen (85% by volume of nitrogen, 15% by volume of oxygen and 10% by volume of methane) is fed into the chamber; the pressure therein is set at $2 \times 10^{-3}$ mm Hg and a first sublayer of the external decorative layer is deposited from titanium carboxynitride. When the thickness of this sublayer reaches 3 μm, the supply of the above-specified gas mixture is stopped and a gas mixture of nitrogen and oxygen (90% by volume of nitrogen and 10by volume of oxygen) is supplied, its pressure is set at $5 \times 10^{-3}$ mm Hg and a second sublayer of the external decorative layer is deposited from titanium oxynitride. When this sublayer thickness reaches 3 μm, the plasma sources are switched-off, the supply of the gas mixture is discontinued, the negative voltage is removed from the prosthesis and the turning device is stopped. 10 minutes afterwards the prosthesis is withdrawn from the chamber.

The resulting prosthesis has the microhardness of 2,500 kgf/mm$^2$, a good adherence between the layers and a colour corresponding to that of a high-quality gold alloy.

The thus-manufactured prosthesis has been fixed in the patient's mouth cavity by means of a bisphate cement. Observations during two years revealed no local or general negative effects on the patient's organism.

The prosthesis colour remained unchanged.

EXAMPLE 17

A dental prosthesis is made in the form of a soldered bridge-like structure comprising a base from a chromium- nickel stainless steel and a silver-cadmium solder with an external decorative layer from a mixture of nitrides of titanium and zirconium (67% by weight of titanium nitride and 33% by weight of zirconium nitride) and an additional layer from cobalt.

The prosthesis base is manufactured and washed as described in Example 11.

Then the base is placed into an electroplating bath for deposition of the additional cobalt layer. As the aqueous solution for the layer deposition use is made of the following composition, g/l: cobalt sulphate - 500, sodium chloride - 17, boric acid - 45. The deposition of the additional cobalt layer is carried out at the current density of 3 A/cm$^2$, the electrolyte temperature of 45° C., pH=4. The additional cobalt layer is deposited to the thickness of 8 $\mu$m.

Then the resulting base with the additional cobalt layer is polished by means of fine pastes. Thereafter the base is washed and placed into a vacuum chamber as described in Example 1.

Then the external protective-decorative layer is deposited as described in Example 9; the deposition is carried out to the layer thickness of 25 $\mu$m. When the thickness of the external decorative layer reaches 25 $\mu$m, the deposition process is discontinued as described in Example 9.

Technical and medical characteristics of the thus-produced prosthesis correspond to the values specified in Example 4.

EXAMPLE 18

A dental prosthesis is made in the form of a soldered bridge-like structure comprising a base from a chromium-nickel stainless steel and a silver-cadmium solder with an external decorative layer from titanium oxynitride and an additional layer of molybdenum.

The prosthesis base is manufactured and washed as described in Example 11.

Then the prosthesis base is placed into a vacuum chamber on a drum of a rotating device.

The vacuum chamber is provided with three plasma sources; in one of them as the material to be evaporated use is made of molybdenum, in the other two - titanium.

The vacuum chamber is evacuated to the pressure of $2 \times 10^{-5}$ mm Hg, the turning device is switched-on, the negative voltage of 600 V is applied to the base, the plasma source of molybdenum is switched-on and its arc current is set at 130 A, whereafter ion purification of the base is carried out for 3 minutes. Then the negative voltage of 25 V is applied to the base and the additional layer of molybdenum is deposited to the thickness of 5 $\mu$m.

Afterwards, plasma sources of titanium are switched-on, arc current values therein are set at 90 A, the plasma source of molybdenum is switched-off and to the base with the additional molybdenum layer the negative voltage of 200 V is applied. Then a gas mixture of nitrogen and oxygen (80% by volume of nitrogen and 20% by volume of oxygen) Is fed into the vacuum chamber, the pressure of the gas mixture is maintained at $5 \times 10^{-3}$ mm Hg and the external decorative layer is deposited from titanium oxynitride to the thickness of 15 $\mu$m.

The resulting prosthesis has technical and medical characteristics similar to those mentioned in Example 2.

EXAMPLE 19

A dental prosthesis is made in the form of a soldered bridge-like structure comprising a base from a chromium-nickel stainless steel and a silver-cadmium solder with an external decorative layer from a mixture of nitrides of titanium and zirconium (30% by weight of titanium nitride and 70% by weight of zirconium nitride) and an additional layer of zirconium.

The prosthesis base is manufactured, polished and washed as described in Example 11 hereinbefore.

Then the base is placed into a vacuum chamber on a drum of a turning device.

The vacuum chamber is provided with three plasma sources; in one of them titanium is used as the evaporated material, in other two - zirconium.

The vacuum chamber is evacuated to the pressure of $1.10^{-5}$ mm Hg, the turning device is switched-on, the negative voltage of 900 V is applied to the base, the plasma source of zirconium is energized and the arc current therein is set at 80 A. The ionic purification of the base is effected for 3 minutes by way of bombardment with zirconium ions. Then the negative voltage of 50 V is applied to the base, the second plasma source with zirconium is switched-on and the arc current therein is set at 80 A, whereafter an additional layer is deposited from zirconium to the thickness of 3 $\mu$m. Then the external decorative layer is deposited from a mixture of nitrides of titanium and zirconium following the procedure described in Example 6.

Technical and medical characteristics of the prosthesis correspond to those described in Example 6.

EXAMPLE 20

A dental prosthesis is made in the form of a soldered bridge-like structure comprising a base from a chromium-nickel stainless steel and a silver-cadmium solder with an external decorative layer from zirconium nitride and additional layer from molybdenum nitride.

The prosthesis base is manufactured, polished and washed as described in Example 11.

Then the base is placed into a vacuum chamber on a drum of a turning device.

The vacuum chamber is provided with three plasma sources; in one of them as the evaporated material use is made of molybdenum, in other two - zirconium.

The vacuum chamber is then evacuated to the pressure of $2 \times 10^{-5}$ mm Hg, the turning device is switched-on, the negative voltage of 600 V is applied to the base, the plasma source of molybdenum is switched-on and the arc current therein is set at 130 A. For 3 minutes an ionic purification of the base is effected by way of bombardment with molybdenum ions.

Then the negative voltage of 25 V is applied to the base, nitrogen is admitted into the chamber and its pressure is maintained at $8 \times 10^{-4}$ mm Hg and an additional layer of molybdenum nitride is deposited to the thickness of 5 $\mu$m. When the additional layer reaches the thickness of 5 $\mu$m, the plasma sources of zirconium are switched-on and the arc current values thereof are set at 90 A in each, the plasma source of molybdenum is switched-off, the negative voltage of 200 V is applied to the base and nitrogen is fed into the chamber so that its pressure is maintained at $4 \times 10^{-3}$ mm Hg. The external decorative layer from zirconium nitride is thus deposited to the thickness of 15 μm.

The resulting external decorative layer has the microhardness of 2,500 kgf/mm$^2$, colour of high-quality gold alloys and a good adhesion.

The thus-produced prosthesis is fixed in the patient's mouth cavity by means of bisphate cement. Observations for three years revealed no local or general negative effects on the patient's organism. The prosthesis did not change its colour. During the observation period no peeling at the soldering points or darkening of the layer at the soldering points was observed.

EXAMPLE 21

A dental prosthesis is made in the form of a soldered bridge-like structure comprising a base from a chromium-nickel stainless steel and a silver-zinc solder with an external decorative layer from titanium nitride, a transition layer from a mixture of chromium and chromium nitride and an additional layer from nickel.

The prosthesis base is manufactured, polished and washed as described in Example 11 hereinbefore.

Then the base is placed into an electroplating bath for deposition of the additional layer of nickel. As the aqueous solution for deposition of this layer use is made of the following composition, g/l: nickel sulphate - 300, magnesium sulphate 50, sodium chloride - 10, boric acid 30.

The process of the layer deposition is carried out at the electrolyte temperature of 40° C., current density of 3 A/dm$^2$ and pH of 4.0.

After deposition of the additional layer of the thickness of 4 μm the prosthesis is washed with running water and polished.

Then the base is placed into a vacuum chamber on a drum of a turning device.

The vacuum chamber is provided with three plasma sources; in one of them as the evaporated material use is made of chromium, in the other two - titanium. Then the transition layer is deposited from a mixture of chromium and chromium nitride to the thickness of 5 μm as described in Example 14.

Thereafter the external decorative layer is deposited from titanium nitride to the thickness of 8 μm. The deposition process is discontinued as described in Example 1. 10 minutes afterwards the prosthesis is withdrawn from the chamber.

The thus-produced prosthesis has technical and medical characteristics similar to those of the prosthesis described in Example 1.

EXAMPLE 22

A dental prosthesis is made in the form of a soldered bridge-like structure comprising a base from a nickel-chromium stainless steel and a silver-cadmium solder with an external decorative layer consisting of two sublayers; one of them adjacent to the base consists of a mixture of cyanonitrides of titanium and zirconium (67% by weight of titanium cyanonitride and 33% by weight of zirconium cyanonitride) and the second sublayer consists of a mixture of nitrides of titanium and zirconium (67% by weight of titanium nitride and 33% by weight of zirconium nitride) and an additional layer of chromium.

The prosthesis base is manufactured and washed as described in Example 11.

Then the base is placed into an electroplating bath and the additional layer of chromium with the thickness of 5 μm is deposited as described in Example 11.

Then the base with the deposited additional layer is polished, washed and put into a vacuum chamber as described in Example 11. The vacuum chamber is provided with three plasma sources; in one of them as the evaporated material use is made of zirconium, in two others - titanium.

The ionic purification of the base with the additional layer of chromium is effected by way of bombardment with zirconium ions as described in Example 6.

Then the transition layer is deposited from a mixture of titanium and titanium nitride as described in Example 12.

Thereafter the negative voltage of 220 V is applied to the base, the plasma sources of titanium are switched-on and the arc current values in each of the three plasma sources are set at 90 A. Then, a gas mixture of nitrogen and acetylene (90% by volume of nitrogen and 10% by volume of acetylene) is introduced into the vacuum chamber, the pressure in the chamber is maintained at $1 \times 10^{-3}$ mm Hg and the first sublayer of the external decorative layer is deposited to the thickness of 9 μm. When the desired thickness value is obtained, the supply of the gas mixture is discontinued and nitrogen is fed into the chamber under the pressure of $5 \times 10^{-3}$ mm Hg and the second sublayer of the external decorative coating is deposited from a mixture of nitrides of titanium and zirconium to the thickness of 4 μm.

Technical and medical characteristics of the thus-produced dental prosthesis are similar to those described in Example 7 hereinbefore.

EXAMPLE 23

A dental prosthesis is made in the form of a soldered bridge-like structure comprising a base from a chromium-nickel stainless steel and a silver-cadmium solder with an external decorative layer consisting of two sublayers; one of them adjacent to the base consists of a mixture of monoxides of titanium and zirconium (33% by weight of titanium monoxide and 67% by weight of zirconium monoxide and the second sublayer consists of a mixture of oxynitrides of titanium and zirconium (33% by weight of titanium oxynitride and 67% by weight of zirconium oxynitride) and an additional layer of chromium nitride.

The prosthesis base is manufactured and washed as described in Example 11 hereinbefore.

Then the base is placed into a vacuum chamber on a drum of a turning device.

The vacuum chamber is provided with four plasma sources; in one of them as the material to be evaporated use is made of chromium, in the second - titanium, in the third and fourth - zirconium. The vacuum chamber is evacuated to the pressure of $2 \times 10^{-5}$ mm Hg, the turning device is switched-on, the negative voltage of 700 V is applied to the base, the plasma source of chromium is energized and the arc current value therein is set at 80 A. The ionic purification of the base by bombardment with chromium ions is effected for 4 minutes.

Thereafter the negative voltage of 30 V is applied to the base, nitrogen is fed into the chamber and its pressure is maintained at $5 \times 10^{-4}$ mm Hg; the additional layer is deposited from chromium nitride to the thickness of 4 μm. When the additional layer reaches the predetermined thickness, two plasma sources of zirconium and one of titanium are switched-on and the arc current values in each of them are set at 90 A, the plasma source of chromium is switched-off and the negative voltage of 200 V is applied to the base with the additional coating from chromium nitride.

Then, the supply of nitrogen into the chamber is discontinued and oxygen is admitted thereinto under the pressure of $3 \times 10^{-4}$ mm Hg and the first sublayer of the external decorative layer is deposited from a mixture of monoxides of titanium and zirconium (33% by weight of titanium monoxide and 67% by weight of zirconium monoxide) to the thickness of 4 μm. Thereafter, the supply of oxygen is terminated and fed into the chamber is a gas mixture of nitrogen and oxygen (82% by volume of nitrogen and 18% by volume of oxygen), the pressure in the chamber is maintained at $5 \times 10^{-3}$ mm Hg and the second sublayer of the external decorative layer is deposited from a mixture of oxynitrides of titanium and zirconium to the thickness of 6 μm.

The resulting external decorative layer has the microhardness of 2,200 kgf/mm², a good adhesion to the transition layer and a colour matching that of a high-quality gold alloy.

The thus-produced prosthesis is fixed in the patient's mouth cavity by means of a bisphate cement. Observations for two years revealed no local or general negative effects on the patient's organism. The layer integrity of the prosthesis was not broken, the prosthesis colour remained unchanged.

EXAMPLE 24

A dental prosthesis is produced in the form of a monolithic bridge-like structure comprising a base from a chromium-nickel alloy with an external decorative layer consisting of three sublayers; one of them adjacent to the base consists of titanium cyanonitride, the second - titanium oxynitride and the third - titanium nitride.

The dental prosthesis base is made, polished, washed and placed into a vacuum chamber as described in Example 1. The vacuum chamber is provided with three plasma sources containing titanium as the material to be evaporated.

The ionic purification of the base is effected by bombardment with titanium ions as described in Example 1.

Then, the negative voltage of 220 V is applied to the base, the plasma sources are switched-on and the arc current in each of them is set at 90 A. Thereafter fed into the chamber is a gas mixture of nitrogen and acetylene (90% by volume of nitrogen and 10% by volume of acetylene); the gas mixture pressure is maintaied at $5 \times 10^{-4}$ mm Hg and the first sublayer of the external decorative layer is deposited from titanium cyanonitride to the thickness of 4 μm.

Then, the supply of the above-mentioned gas mixture is discontinued and a gas mixture of nitrogen and oxygen (82% by volume of nitrogen and 18% by volume of oxygen) is fed into the chamber; the gas mixture pressure in the chamber is maintained at $1 \times 10^{-3}$ mm Hg and the second sublayer of the external decorative layer is deposited from titanium oxynitride to the thickness of 4 μm.

Thereafter, the supply of this gas mixture into the chamber is discontinued and nitrogen is fed thereinto under the pressure of $5 \times 10^{-3}$ mm Hg and the third sublayer of the external decorative layer is deposited from titanium nitride to a thickness of 5 μm.

The resulting external decorative layer has the microhardness of 2,500 kgf/mm², a high adhesion to the base and a colour corresponding to that of a high-quality gold alloy.

The thus-produced prosthesis was fixed in the patient's mouth cavity. Observations for two years revealed no local or general negative effects on the patient's organism. The prosthesis colour remained unchanged. No breaking of the layer integrity was observed.

Sufficiently broad and profound medico-biological investigations have been carried out for the majority of the embodiments of the dental prostheses according to the present invention, which investigations have been extended to the scale of clinical tests.

The study was carried out in the following main areas:

1. Sanitary-chemical studies by tracing migration of the dental prosthesis metals into the model media.

2. Testing the effect of the material of layers and their combinations in the prosthesis on microorganisms, microflora of the mouth cavity and growth of cultures of a live tissue.

3. Histological and histochemical study of the reactions of the organism tissues around the implantant with the test coating (material).

4. Studying the functional state of the animal organism with the implantant:
characteristics of general reactivity;
body mass dynamics;
amount of histamine in blood;
content of Vitamin C in blood;
resistance of functional loads;
state of the central nervous system;
functions of liver and kidney.

5. Histological and histochemical study of the inner organs (liver, kidney, spleen, heart, adrenal glands).

6. Clinical tests of the structures of the dental prostheses according to the present invention.

The above-given program of investigations has been fulfilled, in respect of the majority of structures of the dental prostheses according to the present invention, to its full scope and with positive results obtained. As regards the remaining types of the structures of dental prostheses according to the present invention, the program is in the stage of completion with positive results foreseen.

What is claimed is:

1. A dental prosthesis comprising a base of a durable corrosion-resistant metallic alloy and at least one external decorative layer of a harder material than the base comprising compounds of metals of the subordinate subgroup of Group IV of the periodic system selected from the group consisting of nitrides, oxynitrides, carboxynitrides, cyanonitrides and monoxides of these metals and mixtures of said compounds, the thickness ratio of said external decorative layer to the base being equal to 1:10-200 respectively.

2. A dental prosthesis as claimed in claim 1, wherein as the material of the external decorative layer use is made of compounds selected from the group consisting of nitrides, oxynitrides, carboxynitrides, cyanonitrides and monoxides of titanium and zirconium.

3. A dental prosthesis as claimed in claim 1, wherein between the prosthesis base and the external decorative layer a protective layer is interposed consisting of a metal more electronegative than the material of the external decorative layer and possessing the ability of being passivated in liquid media of the mouth cavity, the thickness ratio of the protective layer to the external decorative layer being equal to 0.3-1:1 respectively.

4. A dental prosthesis as claimed in claim 1, wherein as the metal of the protective layer use is made of a metal selected from the group consisting of titanium, tantalum and chromium.

5. A dental prosthesis as claimed in claim 1, wherein between the external decorative layer and the dental prosthesis base a transition layer is interposed comprising a substance selected from the group consisting of titanium, tantalum and chromium in a mixture with a corresponding nitride at a changing concentration of the nitride across the transition layer thickness within the range of from 0.01 to 90–99.9% by weight, the thickness ratio of the transition layer to the external decorative layer being 0.3-1:1 respectively.

6. A dental prosthesis as claimed in claim 3, wherein between the external decorative layer and the protective layer a transition layer is interposed comprising a substance selected from the group consisting of titanium, tantalum and chromium in a mixture with a corresponding nitride at a changing concentration of the nitride across the transition layer thickness within the range of from 0.01 to 90–99.9% by weight, the thickness ratio of the transition layer to the external decorative layer being 0.3-1:1 respectively.

7. A dental prosthesis as claimed in claim 1, wherein in the case where the prosthesis base comprises a structure of soldered members of a durable corrosion-resistant metallic alloy, between the external decorative layer and the dental prosthesis base an additional layer is interposed consisting of a substance selected from the group covering cobalt, nickel, chromium, molybdenum, zirconium, chromium nitride and molybdenum nitride, the thickness ratio of the additional layer to the external decorative layer being equal to 0.5-1:1 respectively.

8. A dental prosthesis according to claim 5, wherein in the case where the prosthesis base comprises a structure of soldered members from a durable corrosion-resistant metallic alloy, between the transition layer and the dental prosthesis base an additional layer is provided from a substance selected from the group consisting of cobalt, nickel, chromium, molybdenum and zirconium, the thickness ratio of the additional layer to the external decorative layer being equal to 0.5-1:1 respectively.

9. A method for making the dental prosthesis as claimed in claim 7, comprising manufacture of a base of the dental prosthesis by soldering members of the dental prosthesis from a durable corrosion-resistant metallic alloy into an integrated structure; coating the zone of the soldered juncture of this structure or the entire structure, by electroplating, with an additional layer of a substance selected from the group consisting of cobalt, nickel, chromium, molybdenum, zirconium, chromium nitride and molybdenum nitride; deposition of an external decorative layer by vacuum technique, the thickness ratio of the additional layer to the external decorative layer being equal to 0.5-1:1 respectively.

10. A method of making the dental prosthesis as claimed in claim 7, comprising manufacture of a base of the dental prosthesis by soldering members of the dental prosthesis from a durable corrosion-resistant metallic alloy into an integrated structure; coating the zone of the soldered juncture of said structure of the entire structure, by vacuum technique, with an additional layer of a substance selected from the group consisting of cobalt, nickel, chromium, molybdenum, zirconium, chromium nitride and molybdenum nitride; deposition of an external decorative layer by vacuum technique, the thickness ratio of the additional layer to the external decorative layer being equal to 0.5-1:1 respectively.

* * * * *